United States Patent [19]

Olsen

[11] 4,190,153
[45] Feb. 26, 1980

[54] SPONGE DISPOSAL TRAY

[75] Inventor: C. Eric Olsen, Ventura, Calif.

[73] Assignee: California Medical Developments, Inc., Ventura, Calif.

[21] Appl. No.: 953,697

[22] Filed: Oct. 23, 1978

[51] Int. Cl.² .......................... B65D 1/36; B65D 81/36
[52] U.S. Cl. ................................... 206/362; 206/63.5; 206/525; 206/438; 229/2.5 R; 229/28 R
[58] Field of Search ................. 206/361, 362, 63.5, 206/515, 634, 531, 532, 526, 438, 497; 229/2.5 R, 28 R, 15

[56] References Cited

U.S. PATENT DOCUMENTS

| 2,553,232 | 5/1951 | Beyer | 206/63.5 |
|---|---|---|---|
| 3,389,825 | 6/1968 | Whiteford | 206/526 |
| 3,390,766 | 7/1968 | Stockdale | 229/28 R |
| 3,895,713 | 7/1975 | Bunnell | 229/15 |
| 3,899,080 | 8/1975 | Brunda | 206/634 |
| 3,921,804 | 11/1975 | Testor | 206/515 |
| 4,054,207 | 10/1977 | Lazure et al. | 229/2.5 R |

FOREIGN PATENT DOCUMENTS 1183454  3/1970  United Kingdom ................. 206/497

Primary Examiner—William T. Dixson, Jr.
Attorney, Agent, or Firm—Jack C. Munro

[57] ABSTRACT

A sponge disposal tray for use in conjunction with medical surgical procedures which comprises a plurality of containers which are normally closed by a thin sheet material access cover. The access cover includes a plurality of access openings with a single access opening connecting with a single container. Each access opening comprises a pair of crossed slits which is normally closed but openable upon insertion of a single sponge into a container. A removable sealing cover is to be adhesively secured to the frame and to completely cover said access cover. The frame may include a sponge storage compartment. Also the bottom surface of each of the containers may include an adhesive layer to facilitate frictional connection of the tray to a supportive surface.

4 Claims, 2 Drawing Figures

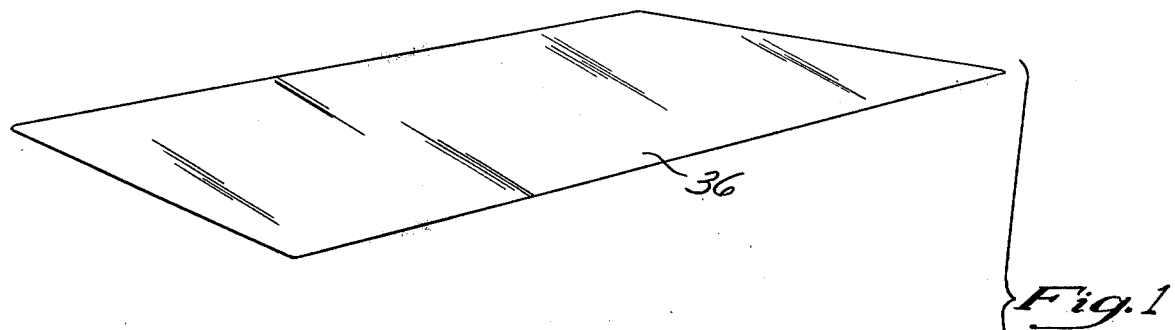
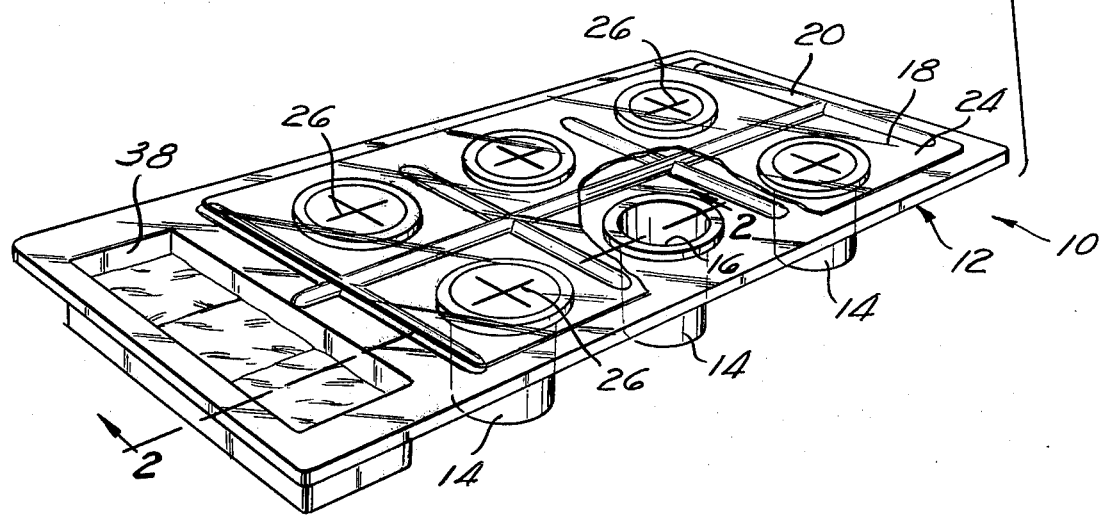
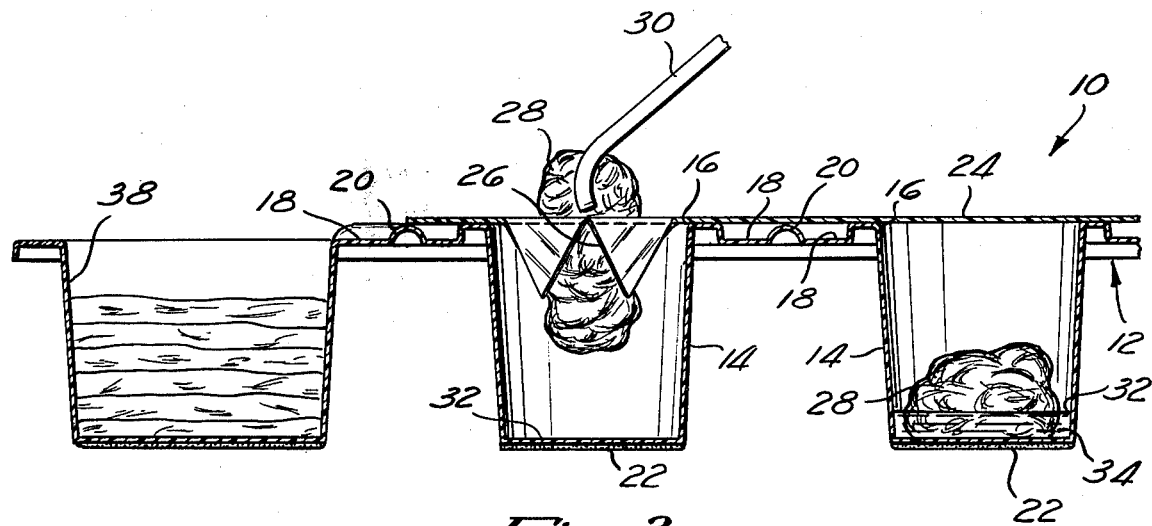

SPONGE DISPOSAL TRAY

BACKGROUND OF THE INVENTION

The field of this invention relates to medical devices and more particularly to a tray which facilitates the location of used sponges after such has been used to absorb blood during a surgical operation.

During the performing of surgery, it is most common to use a small gauze pad, which is commonly referred to as a sponge, to absorb blood. The bleeding by the patient obscures the surgical procedure by the physician. Therefore these sponges are used to remove the accumulated blood and therefore permit the surgical procedure to proceed.

Up to the present time, there has been no known method to accurately ascertain the amount of blood lost. If such amount could be ascertained, the precise amount of blood can be replaced to the patient in transfusions.

Additionally, a necessary requirement is to physically count each and every item which enters the surgery room and after the surgery the items are again counted to make sure that no foreign object remains within the patients body. For example, if fifty in number of sponges have been employed during the surgical procedure, each of the used sponges must be individually accounted for. Prior to this invention there has been no means which facilitated the counting of these sponges when used since they are normally placed in bulk within some form of a container.

SUMMARY OF THE INVENTION

The structure of this invention is summarily described within the Abstract of the Disclosure and reference is to be had thereto.

The primary objective of this invention is to construct a tray which facilitates the disposing of sponges which have been used to absorb blood from a surgical procedure. The sponges can be quickly and easily counted. Also the amount of liquid in total that the sponges have absorbed can be readily ascertained to thereby more accurately calculate the amount of blood to be replaced within the patient to bring the patient to his normal blood level.

A further advantage of this invention is that the tray is constructed of few easily assembled parts to thereby be inexpensive and thereby facilitate disposing of the tray after a single use.

BRIEF DESCRIPTION OF THE DRAWING

FIG. 1 shows an exploded isometric view of the tray of this invention; and

FIG. 2 is a cross-sectional view through the tray of this invention taken along line 2—2 of FIG. 1.

DETAILED DESCRIPTION OF THE SHOWN EMBODIMENT

Referring particularly to the drawing there is shown in FIG. 1 the tray 10 of this invention which takes the form of a plastic planar frame 12 which is constructed of sheet material. The frame 12 includes a plurality (six in number being shown) integrally formed containers 14. The containers 14 are also constructed of a thin plastic sheet material. Each of the containers 14 are located evenly spaced apart and each include at the upper end thereof an access opening 16. Located about each of the containers 14 and within the frame 12 is a recessed area 18 which is interspersed with elongated ribs 20. The ribs 20 accompanied by the recesses 18 provide regidity to the frame 12.

The exterior bottom surface of each of the containers 14 is located in the same plane. To this bottom surface of each container 14 is located a layer of frictionally grabbing material such as a dry adhesive 22. With the tray 10 located upon a supportive surface (not shown), the adhesive 22 will function to frictionally adhere to the supportive surface and therefore prevent any undesirable movement on the supportive surface.

Adhesively secured or otherwise secured to the upper surface of the frame 12 is a thin sheet material access cover 24. The access cover 24 is to cover each of the access openings 16. The access cover 24 will normally be constructed of a transparent material with it also being understood that the containers 14 as well as the frame 12 will be constructed of a transparent material.

Within the access cover 24 is located a plurality of crossed slits 26. There is to be a crossed slit arrangement 26 for each container 14. The crossed slit arrangement 26 will assume a normally closed condition as shown in FIG. 1 of the drawing. A used sponge 28 is to be inserted by means of a forceps 30 into the chamber 32 within a particular container 14 by being conducted through the access opening provided by its particular crossed slit arrangement 26. This is shown clearly within FIG. 2 of the drawing. Upon location of the sponge 28 within the chamber 32 and the forceps 30 being removed, the particular crossed slit arrangement 26 thereby recloses.

Also shown within FIG. 2 of the drawing is a sponge 28 positioned within a container 14 with its particular crossed slit arrangement 26 closed. It is to be noted that there is a small amount of liquid 34 located within the chamber 32 which has drained from the sponge 28.

In order to protect the entry of foreign materials through the access openings 26 and into the chambers 32 prior to use of the tray 10, a protective cover 36 is to be adhesively secured to the peripheral edge of the frame 12. This protective cover 36 is to be manually peeled off of the surface of the frame 12 when it is ready to employ the use of the tray 10. The protective cover 36 will be normally constructed of a thin flexible plastic material.

It may be desirable to provide with each tray 10 a quantity of the sterile sponges, one each of which when used is to be located within a container 14. For this purpose, a compartment 38 is integrally attached to the frame 12 and is to provide storage for a pad of sponges. The sealing cover 36 is to close compartment 38 and to maintain the sterility of the sponges prior to use.

In the operation of the structure of this invention, the number of the trays 10 which are estimated to be required to be used within the surgical operation are located within the surgical operating room. It is to be normally envisioned that each tray 10 will include ten in number of the containers 14 (although only six is to be shown within the drawing). It appears that ten is the most convenient number but it is to be within the scope of this invention that any number of containers 14 could be employed.

The operator, such as a nurse, will then remove the sealing cover 36 from one or more of the trays 10. Each sterile sponge after it is used to absorb blood is then inserted within a single compartment 32 with it being understood that only a single sponge would be located within a single compartment 32. At the end of the surgical procedure, the gross weight of the trays 10 is calculated with the beginning weight being subtracted therefrom. Therefore the gross weight of liquid lost can be ascertained which can then be employed to determine the volume of blood loss and facilitate replacement of a precise quantity of blood within the patient.

Also at the end of the surgical operation, the nurse or other appropriate individual can readily ascertain the exact number of sponges used to account for each and every sponge. The counting procedure is facilitated since the containers 14 are constructed of a transparent material and therefore observance of each of the used sponges is readily facilitated.

What is claimed is:

1. A medicinal sponge disposal tray comprising:
   a transparent frame;
   a plurality of initially empty containers, each said container being integral with said frame, each said container having an open upper end;
   a thin sheet material transparent access cover located over each of said open upper ends and fixedly secured to said frame, said access cover including a plurality of slitted access openings with there being a single access opening connecting with each said open upper end of a said container, each said access opening being normally closed to enclose said empty container but being openable to permit insertion and deposit of a sponge into a said container and being automatically reclosable thereafter, entry into each container being only through its respective said slitted access opening; and
   a thin sheet material sealing cover covering said access cover, said sealing cover preventing entry of foreign material through said access openings into said containers, said sealing cover being discardable to expose said access cover.

2. The tray as defined in claim 1 including:
   a frictionally binding layer of material being attached to the exterior bottom surface of each said container, whereby said frictionally grabbing layer of material prevents undesirable movement of said tray upon a supportive surface.

3. The tray as defined in claim 2 including:
   a sponge storage compartment attached to said frame, said sponge storage compartment to facilitate storage of a quantity of sterile sponges for use in conjunction with said containers of said tray.

4. The tray as defined in claim 1 including:
   a sponge storage compartment attached to said frame, said sponge storage compartment to facilitate storage of a quantity of sterile sponges for use in conjunction with said containers of said tray.

* * * * *